United States Patent [19]

Aileo et al.

[11] Patent Number: 5,020,163
[45] Date of Patent: Jun. 4, 1991

[54] EARSEAL FOR SOUND-ATTENUATING EARCUP ASSEMBLY

[75] Inventors: Jackson A. Aileo, Carbondale; Richard J. Long, Lake Ariel, both of Pa.

[73] Assignee: Gentex Corporation, Carbondale, Pa.

[21] Appl. No.: 376,125

[22] Filed: Jun. 29, 1989

[51] Int. Cl.⁵ .............................................. A42B 1/06
[52] U.S. Cl. ..................................... 2/209; 381/183; 181/129
[58] Field of Search ............... 2/209, 423, 6; 381/183, 381/187; 181/129

[56] References Cited

U.S. PATENT DOCUMENTS 3,593,341  7/1971  Aileo ........................................ 2/209
3,875,592  4/1975  Aileo ........................................ 2/209
3,938,614  2/1976  Ahs .......................................... 2/209
4,856,118  8/1989  Sapiejewski ............................ 2/209

Primary Examiner—Peter Nerbun
Attorney, Agent, or Firm—Shenier & O'Connor

[57] ABSTRACT

A resilient annular earseal for sealing the region between an earcup shell and a wearer's head is formed with an aperture for receiving the wearer's ear and has an outer peripheral portion projecting a predetermined first distance toward the wearer's head and an inner peripheral portion projecting a predetermined second distance toward the wearer's head that is appreciably greater than the first distance. Since the inner peripheral portion contacts the wearer's head along a strip that is closer to the ear, and hence more predictable in its three-dimensional contour, it forms an effective seal around the entire periphery of the ear.

14 Claims, 3 Drawing Sheets

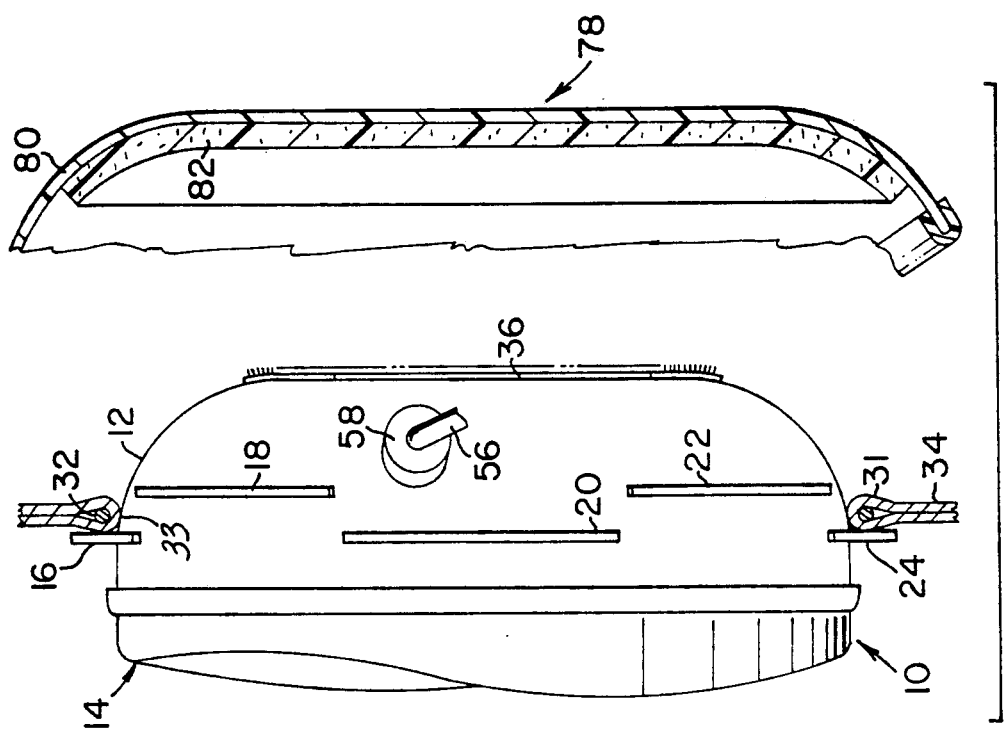
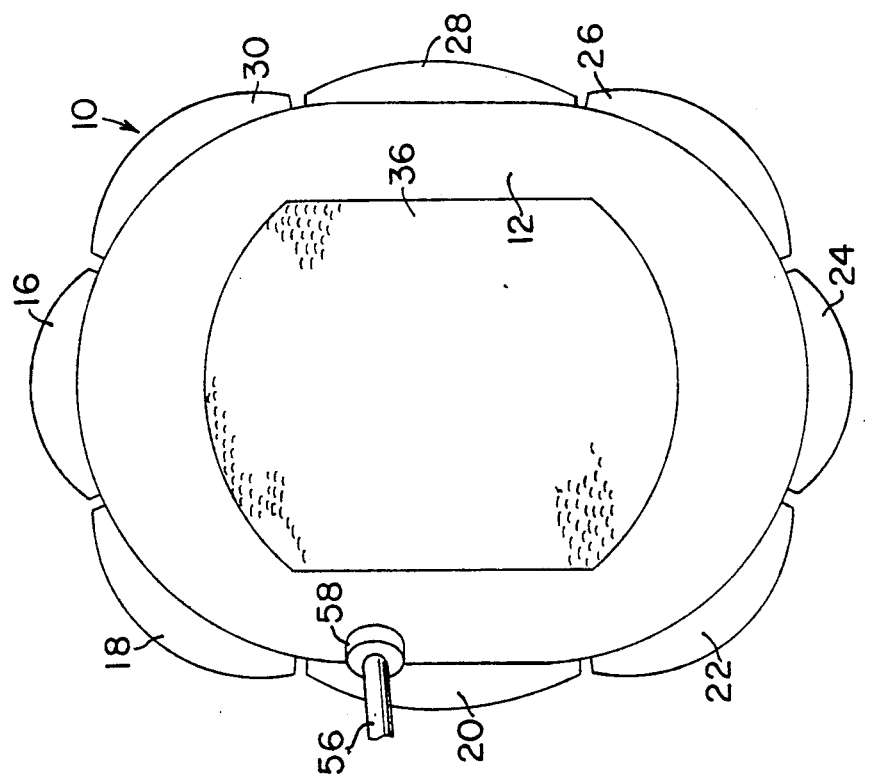

EARSEAL FOR SOUND-ATTENUATING EARCUP ASSEMBLY

BACKGROUND OF THE INVENTION

This invention relates to a compliant earseal for sealing the region between the earcup shell of a sound-attenuating earcup assembly and a wearer's head, as well as to an earcup assembly incorporating such a seal.

Earcup assemblies for attenuating ambient sound in noisy environments, such as in or around military helicopters or other aircraft, are known in the art. Such assemblies are shown, for example, in U.S. Pat. Nos. 3,190,973, 3,470,564, 3,875,592 and 3,943,572, issued to applicant Jackson A. Aileo and owned by the assignee herein. As shown in the first patent identified above, the earcups of such assemblies may house earphones to allow communication or monitoring of the ambient sound.

Earcup shells of the prior art conventionally comprise a shell fitted with a planar annular flange for receiving a compliant earpad or earseal. One of the problems experienced with such earcups of the prior art is that, because of the nonplanar contour of the head in the region of the ear, the earpad does not form an effective seal around the entire periphery of the pad without excessive pressure. Previous expedients have included forming the flange with a complementary contour to assure a better match between the earseal and the wearer's head. While this expedient ameliorates the situation somewhat, it does not overcome the fact that the facial contours of different individuals, and hence the complementary matching contours, vary widely.

SUMMARY OF THE INVENTION

One of the objects of our invention is to provide an earseal that effectively seals the region between the earcup shell of a sound-attenuating earcup assembly and the wearer's head.

Another object of our invention is to provide an earseal that is comfortable.

A further object of our invention is to provide an earseal that accommodates a wide range of head shapes and sizes.

Still another object of our invention is to provide an earseal that is compatible with earcups of existing assemblies.

Other and further objects will be apparent from the following description.

In general, our invention contemplates a resilient earseal for sealing the region between an earcup shell and a wearer' head which is formed with an aperture for receiving the wearer's head and has an outer peripheral portion projecting a predetermined first distance toward the wearer's head and an inner peripheral portion projecting a predetermined second distance toward the wearer's head that is appreciably greater than the first distance. Preferably the seal is used in combination with an earcup shell having an inwardly extending flange for supporting the earseal, the flange being preferably coextensive with the outer and inner peripheral portions of the seal. Preferably the earseal comprises a first resilient element of predetermined width and a second resilient element of predetermined lesser width overlying the inner periphery of the first element.

Since the inner peripheral portion is located inwardly relative to the outer peripheral portion of the earseal, the inner portion contacts the wearer's head along a strip that is closer to the ear and hence more predictable in its three-dimensional contour. Since the inner peripheral portion projects appreciably beyond the outer peripheral portion, it sustains a substantial portion of the clamping force between the earcup shell and the wearer's ear and hence forms an effective seal.

BRIEF DESCRIPTION OF THE DRAWINGS

In the accompanying drawings to which reference is made in the instant specification and which are to be read in conjunction therewith and in which like reference numerals are used to indicate like parts in the various views:

FIG. 4 is a right side elevation of the earcup assembly of FIG. 1 with the earseal and earcup flange removed.

FIG. 5 is a rear elevation of the earcup assembly of FIG. 1 with the earseal removed, showing one form of mounting in a helmet assembly.

DESCRIPTION OF THE PREFERRED EMBODIMENT

FIGS. 1 to 5 show a right earcup assembly, indicated generally by the reference number 10, incorporating an earseal constructed according to our invention. The corresponding left earcup assembly is a mirror image of the right earcup assembly 10 and therefore has not been shown. Earcup assembly 10 includes a generally elliptical cup-shaped rigid shell 12 having an opening for receiving the ear of the wearer. Shell 12 preferably comprises a low-impact grade of plastic, such as acrylonitrile-butadiene-styrene (ABS) terpolymer, which crushes upon impact at an applied force less than that required to crush the skull of the wearer, as described in copending application Ser. No. 07/182,851, filed Apr. 18, 1988, the specification of which is incorporated herein by reference. Preferably, shell 12 is provided on its inner surface with a coating 60 of sound-deadening material, as described in said copending application.

Figure 2:
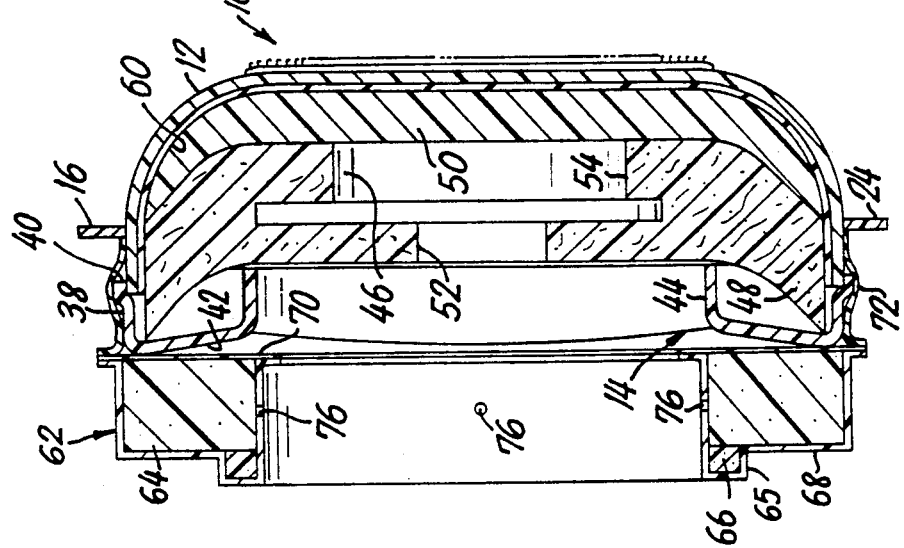
FIG. 2 is a section of the earcup assembly of FIG. 1, taken along line 2—2.

A flange indicated generally by the reference numeral 14 extends inwardly from the periphery of the shell 12 to define an opening for receiving the ear of the wearer. Preferably, flange 14 is formed from the same material as shell 12. Referring particularly to FIG. 2, flange 14 is formed with a peripheral portion 38 which is generally in register with the periphery of shell 12 and is formed with a stepped shoulder portion 40 for receiving said periphery of the shell. Flange 14 also has a portion 42 extending inwardly away from peripheral portion 38 to define a smaller-circumference aperture for receiving the wearer's ear as well as to provide a support for the earseal to be described. Preferably the surface of portion 42 of flange 38 is contoured in a manner complementary to that of the adjacent portion of the wearer's head as described in Aileo U.S. Pat. No. 3,875,592, the specification of which is incorporated herein by reference. Inwardly extending portion 42 of flange 38 in turn has a portion 44 extending in the direction of shell 12 and away from the wearer's ear. Flange 14 is secured to shell 12 by any suitably means such as a layer of cement (not shown) applied along the interface between shoulder 40 and the periphery of the shell. Flange 14 supports an earseal, indicated generally by the reference character 62, that is the subject matter of our invention and is described in detail below.

Earcup assembly 10 contains an earphone 46 of any suitable type known to the art. Earphone 46 fits within a complementary cutout 54 formed in an earphone pad 48 preferably comprising polyurethane foam. A circular aperture 52 formed in the front of earphone pad 48 provides a direct acoustical coupling between earphone 46 and the wearer's ear. A spacer pad 50 also preferably comprising polyurethane foam fills the interior of earcup shell 12 behind pad 48. Referring to FIGS. 4 and 5, a cord 56 from earphone 46 passes through a grommet 58 carried by shell 12 for coupling to an external communication system (not shown).

A plurality of tabs 16, 18, 20, 22, 24, 26, 28 and 30 extending outwardly from earcup shell 12 at circumferentially spaced locations about the periphery thereof define a circumferentially extending, outwardly opening channel. Tabs 16 to 30 are preferably formed of the same material as shell 12 and flange 14. Any suitable means such as cement (not shown) is used to secure tabs 16 to 30 on earcup shell 12. Referring to FIG. 5, the channel formed by tabs 16 to 30 receives a fabric loop 31 surrounding an opening 33 in the side panel of a helmet suspension 34 such as shown, for example, in Aileo U.S. Pat. No. 3,470,564, the specification of which is incorporated herein by reference. A cord 32 disposed in the loop 31 is adapted to be tightened to hold the suspension 34 in engagement with the outer surface of earcup shell 12, as shown in the above-identified patent. Helmet suspension 34 supports a helmet, indicated generally by the reference number 89, having a hard outer shell 80 extending over the earcup assembly 10 as shown in FIG. 5. Shell 80 may comprise any suitable material, such as fiber-glass or a laminate of resin-impregnated layers of aramid cloth sold under the trademark KEVLAR. Shell 80 may optionally carry a polyurethane foam pad 82 opposite earcup assembly 10.

Figure 6:
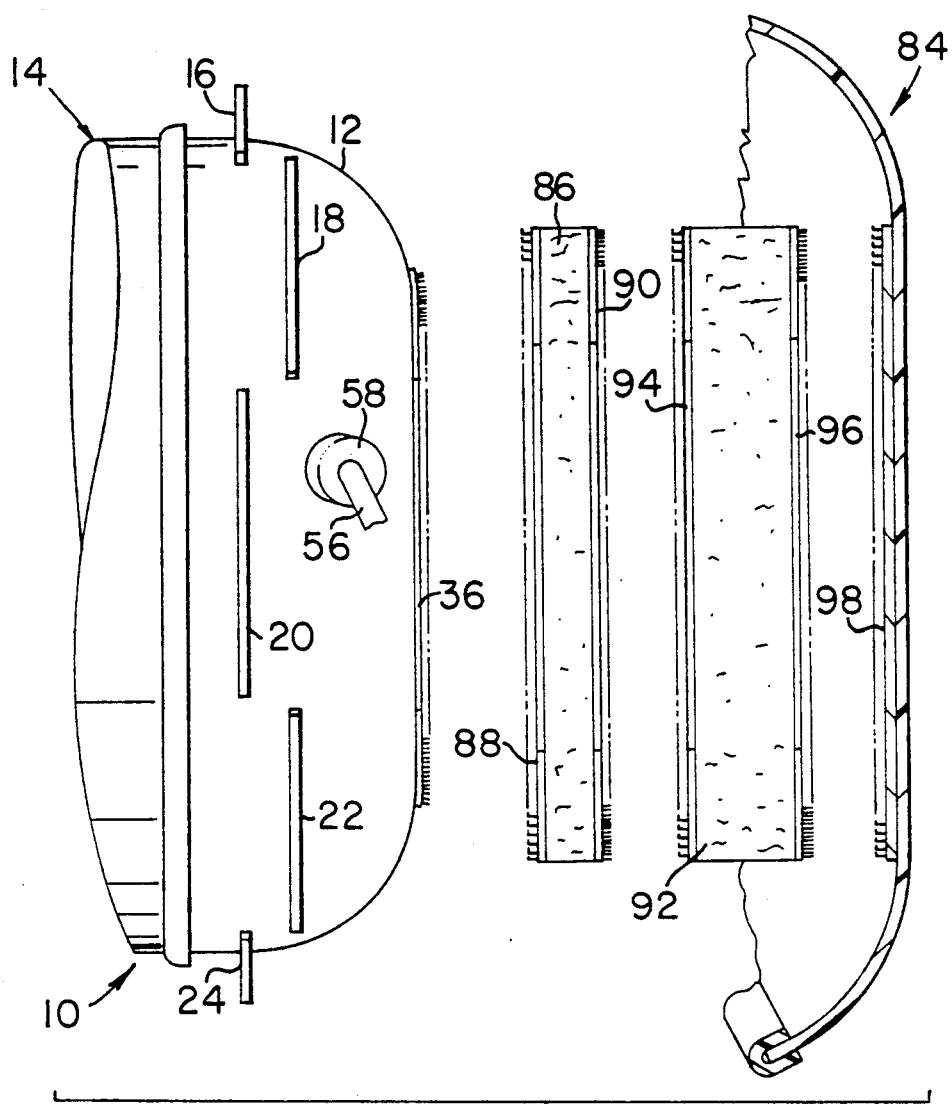
FIG. 6 is a rear elevation of the earcup assembly of FIG. 1 with the earseal removed, showing an alternative form of mounting in a helmet assembly.
Figure 7:
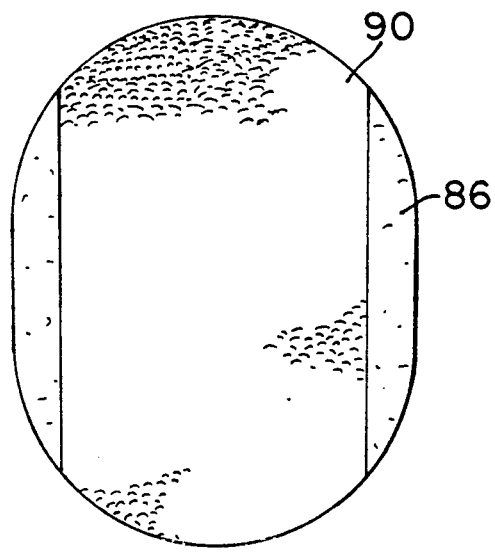
FIG. 7 is a right side elevation of one of the spacer pads of the mounting shown in FIG. 6.

Referring to FIGS. 2, 4 and 5, earcup shell 12 also carries a strip 36 of pile fastener material, such as that sold under the trademark VELCRO, to permit assembly 10 alternatively to be releasably secured to the mounting shown in FIGS. 6 and 7. Strip 36 may be omitted if earcup assembly 10 is only intended for mounting in helmet suspensions, such as the suspension 34 shown in FIG. 5, that engage tabs 16 to 30.

Figure 3:
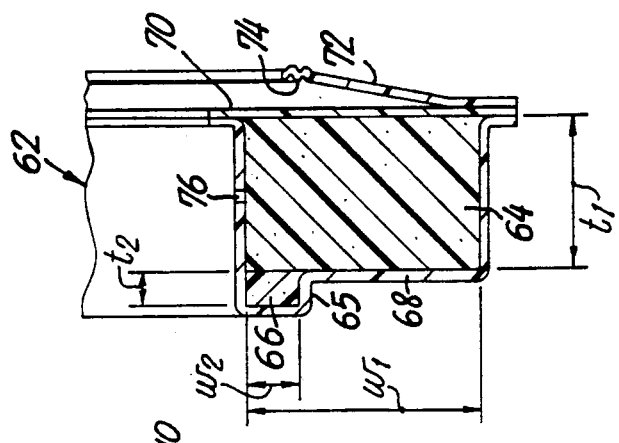
FIG. 3 is an enlarged fragmentary section of the earseal of the assembly of FIG. 1 as it appears when removed from the earcup.
Figure 1:
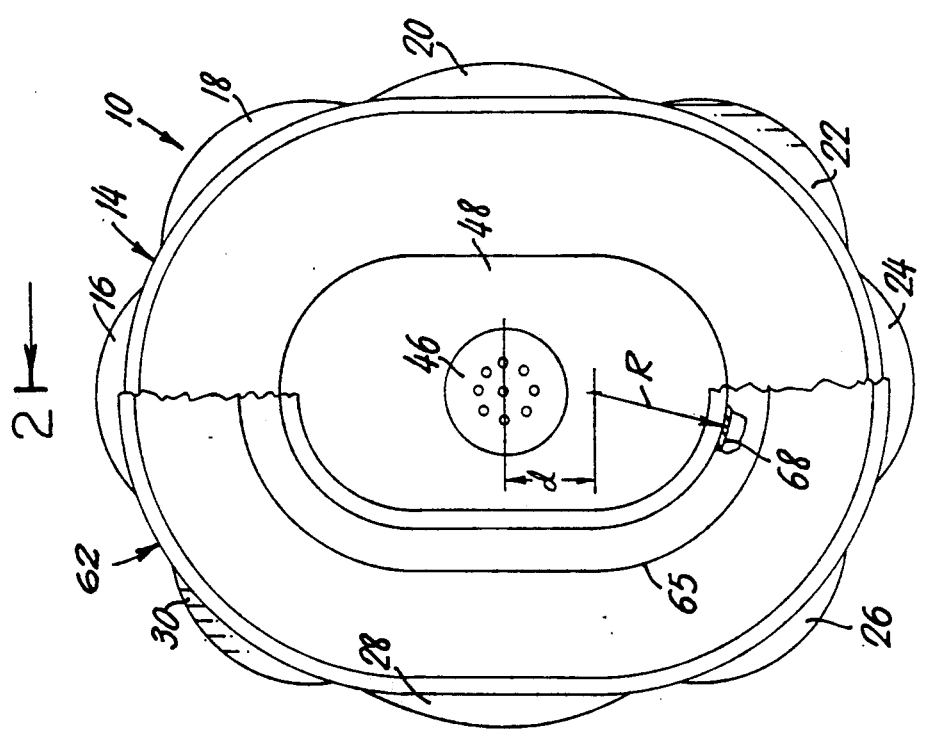
FIG. 1 is a left side elevation of a right earcup assembly incorporating an earseal constructed according to our invention, with parts broken away.

Referring to FIGS. 1 to 3, earseal 62 resiliently seals the region between the wearer's head and earcup 12 and flange 14. Earseal 62, which has the elongated annular shape of flange 14, contains a first resilient foam layer 64 and a second resilient foam layer or ring 66 overlying the inner periphery of layer 64. In the preferred embodiment, as shown in FIG. 3, foam layer 64 is formed with a uniform rectangular cross-section having a width $w_1$ of 25/32 inch and a thickness $t_1$ of ½ inch, while layer 66 is formed with a uniform rectangular cross-section having a width $w_2$ of 3/16 inch and a thickness $t_2$ of ⅛ inch. Layers 64 and 66 each have semicylindrical inner surface portions of radius $R = 1$ inch at the top and bottom of the seal 62, as well as planar inner surface portions of length $2d = 15/16$ inch between the two semicylindrical portions. Preferably, layer 64 comprises an energy-absorbing, slow-recovery polyurethane foam such as Temper Foam Type T-38, while layer 66 comprises a somewhat stiffer material, preferably a unicellular vinyl nitrile foam such as Ensolite Type ALC from Uniroyal.

Foam layers 64 and 66 are encased in an envelope formed from a base 70 and an outer cover 68 of polyurethane film. Cover 68 is preformed in the shape shown in FIGS. 2 and 3. Preferably, cover 68 has a thickness of 0.020 inch while base 70 has a thickness of 0.015 inch. In assembling the parts of earseal 62, the inner and outer surfaces of layer 66 are first tack cemented to the mating surfaces of cover 68 using adhesive (not shown). Tacks of adhesive (not shown) are then applied to the surface portion of layer 64 adjoining layer 66, following which layer 64 is placed on layer 66 and the two parts bonded together. Cover 68 is then bonded to base 70 along the inner and outer peripheries thermally or ultrasonically.

An annular lip 72 having a thickness of 0.015 inch is bonded in a similar manner to the outer periphery of base 70 on the other side from cover 68. Lip 72 is stretched over the periphery of flange 14 to retain earseal 62 on the earcup-flange subassembly. To facilitate assembly of the earseal 62 onto the flange 14, lip 72 is formed with a bead 74 on its inner surface as shown in FIG. 3. Perforations 76 formed at regular intervals about cover 68 vent the interior of earseal 62 to allow air to escape from the interior in response to external pressure. Four 0.025-inch holes 76 are provided in the embodiment shown.

From the foregoing, it will be apparent that earseal 62 has an outer peripheral portion projecting a predetermined first distance $D_1 = t_1$ (neglecting envelope thickness) toward the wearer's ear from flange 14, as well as an inner peripheral portion 65 projecting a predetermined second distance $D_2 = t_1 + t_2$ toward the wearer's ear from flange 14 that is appreciably greater than the first distance $D_1$, the difference $D_2 - D_1$ being equal to $t_2$, the thickness of the foam layer 66. Owing to this differential projection, inner peripheral portion 65 forms an effective seal with the portion of the wearer's head that is closest to the ear and thus most uniform in contour from individual to individual. At the same time, the outer peripheral portion of earseal 62 bears against an annular portion of the wearer's head that is more distant from the ear to enhance the effectiveness of the seal.

Owing to this formation of a more effective seal with the wearer's head, an earcup equipped with earseal 62 provides significantly more attenuation of ambient sounds that similar assemblies lacking the inner ring 66. Thus, comparative tests indicate that the disclosed earcup assembly provides 8.6 dB more attenuation at 500 Hz and 5.7 dB more attenuation at 2 kHz.

FIGS. 6 and 7 show an alternative earcup mounting using hook-and-loop fastener strips rather than the means shown in FIG. 5. More particularly, a modified helmet shell 84 carries on its inner surface a strip 98 of hook-type fastener material, such as that sold under the trademark VELCRO, that releasably adheres to the pile material of strip 98 directly or, as shown in FIG. 6, through one or more spacer pads 86 and 92 which are preferably of different thicknesses to maximize the number of possible spacings. Spacer pad 86, also shown in FIG. 7, carries complementary strips 88 and 90 of hook and pile material similar to that of strips 98 and 36, respectively. Spacer pad 92, which is similar to pad 86 but twice as thick, carries strips 94 and 96 similar to strips 88 and 90, respectively. If desired, there may also be interposed, between earcup 10 and helmet shell 84, the side panel (not shown) of an inner helmet suspension that is similarly provided with hook and pile fastener strips on its opposite surfaces. Such as arrangement is shown in Aileo U.S. Pat. Nos. 4,231,117 and 3,9343,572, the disclosures of which are incorporated herein by reference. If the earcup assembly is intended solely for use in helmets such as helmet 84 having hook and pile fasteners, tabs 16 to 30 may be omitted.

It will be seen that we have accomplished the objects of our invention. Our earseal effectively seals the region between the earcup shell and the wearer's head, while at the same time being comfortable. Our earseal accommodates a wide range of head shapes and sizes and is compatible with earcups of existing assemblies.

It will be understood that certain features and subcombinations are of utility and may be employed without reference to other features and combinations. This is contemplated by and within the scope of our claims. It is further obvious that various changes may be made in details within the cope of our claims without departing from the spirit of our invention. It is, therefore, to be understood that our invention is not to be limited to the specific details shown and described.

Having thus described our invention, what we claim is:

1. An earcup assembly including in combination a shell adapted to fit over a wearer's ear, and a resilient annular earseal for sealing the region between said shell and the wearer'head, said earseal being formed with an aperture for receiving the wearer's ear and having an outer peripheral portion of a predetermined thickness and the wearer's head, said earseal being formed with an thickness, the annular width of the inner peripheral portion being generally less than that of the outer peripheral portion.

2. An earcup assembly as in claim 1 in which said inner peripheral portion has a substantially planar surface portion adapted to contact the wearer's head.

3. An earcup assembly as in claim 1 in which said shell has an inwardly extending flange supporting said ear-seal.

4. An earcup assembly as in claim 3 in which said flange is generally coextensive with said portions of said earseal.

5. An earcup assembly as in claim 1 in which said earseal comprises a first resilient element of predetermined annular width and a second resilient element of generally less than half said width overlying the inner peripheral portion of said first element.

6. An earcup assembly as in claim 5 in which said shell has an inwardly extending flange supporting said first element.

7. An earcup assembly as in claim 6 in which said flange is generally coextensive with said first element.

8. An earcup assembly as in claim 5 in which said first element is thicker than the said second element.

9. A resilient annular earseal for sealing the region between an earcup shell and a wearer's head, said earseal being formed with an aperture for receiving the wearer's ear and having an outer peripheral portion of a predetermined thickness and a projecting inner peripheral portion of a greater thickness, the annular width of the inner peripheral portion being generally less than that of the outer peripheral portion.

10. An earseal as in claim 9 in which said inner peripheral portion has a substantially planar surface portion adapted to contact the wearer's head.

11. An earseal as in claim 9 comprising a first resilient element of predetermined annular width and a second resilient element of generally less than half said width overlying the inner peripheral portion of said first element.

12. An earseal as in claim 11 in which said first element is thicker than said second element.

13. An earseal as in claim 9 including an envelope encasing said portions.

14. An earseal as in claim 13 in which said envelope has an annular lip adapted to be stretched over the periphery of said shell.

* * * * *

UNITED STATES PATENT AND TRADEMARK OFFICE
CERTIFICATE OF CORRECTION

PATENT NO.    : 5,020,163
DATED         : June 4, 1991
INVENTOR(S)   : JACKSON A. AILEO and RICHARD J. LONG It is certified that error appears in the above-identified patent and that said Letters Patent is hereby corrected as shown below:

Column 5, line 31, " , " after "ear" is deleted.

Column 5, line 33, " wearer' " is amended to read - - wearer's --.

Column 5, line 36, "the wearer's head, said earseal being formed with an" is deleted; -- a projecting inner peripheral portion of a greater -- is inserted.

Signed and Sealed this

Third Day of November, 1992

Attest:

DOUGLAS B. COMER

*Attesting Officer*      Acting Commissioner of Patents and Trademarks